(12) United States Patent
Otagiri et al.

(10) Patent No.: US 7,253,259 B2
(45) Date of Patent: Aug. 7, 2007

(54) PROTEIN CONTAINING SERUM ALBUMIN DOMAIN

(75) Inventors: Masaki Otagiri, Kumamoto (JP); Yoshinori Kida, Osaka (JP); Naohisa Katayama, Osaka (JP); Toshiya Kai, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/044,265

(22) Filed: Jan. 28, 2005

(65) Prior Publication Data

US 2005/0256303 A1 Nov. 17, 2005

(30) Foreign Application Priority Data

Mar. 3, 2004 (JP) .............................. 2004-058582

(51) Int. Cl.
*C07K 1/00* (2006.01)
(52) U.S. Cl. ..................................................... 530/350
(58) Field of Classification Search ................. 530/350
See application file for complete search history.

(56) References Cited

U.S. PATENT DOCUMENTS

| | | | |
|---|---|---|---|
| 5,652,352 A | 7/1997 | Lichenstein et al. | 536/23.5 |
| 5,780,594 A | 7/1998 | Carter et al. | 530/363 |
| 6,274,305 B1 * | 8/2001 | Sonnenschein et al. | 435/4 |
| 6,787,636 B1 | 9/2004 | Carter et al. | 530/363 |
| 2003/0161826 A1 * | 8/2003 | Arnason et al. | 424/141.1 |

FOREIGN PATENT DOCUMENTS

| | | |
|---|---|---|
| EP | 0 073 646 A2 | 3/1983 |
| JP | 58-56684 A | 4/1983 |
| JP | 5-292993 A | 11/1993 |

OTHER PUBLICATIONS

Sheffield et al., Modulation of Clearance of Recombinant Serum Albumin by Either Glycosylation or Truncation, Thrombosis Reasearch, 99 (2000), p. 613-621.*
Dockal et al., The Three Recombinant Domains of Human Serum Albumin, J. of Biological Chemistry, 274, 41 (1999), p. 29303-29310.*

* cited by examiner

*Primary Examiner*—Karen Cochrane Carlson
*Assistant Examiner*—Agnes B. Rooke
(74) *Attorney, Agent, or Firm*—Kubovcik & Kubocik

(57) ABSTRACT

A protein produced by gene recombinant technology, including at least one domain selected from domains I, II, and III of serum albumin but having a different structure from that of native albumin; and a method of producing the protein. The protein has an enhanced functional activity or activities selected from among various functional activities or serum albumin including antibacterial activity, antioxidative effect, inflammation inhibitory effect, in vivo substance transporting action, and enzymatic activity.

4 Claims, 4 Drawing Sheets

( ) REPRESENTS A DNA SEQUENCE OF HSA BEFORE THE INTRODUCTION OF VARIATION.

( ) REPRESENTS A DNA SEQUENCE OF HSA BEFORE THE INTRODUCTION OF VARIATION.

( ) REPRESENTS A DNA SEQUENCE OF HSA BEFORE THE INTRODUCTION OF VARIATION.

SEQUENCE LISTING

```
<160> NUMBER OF SEQ ID NOS: 11

<210> SEQ ID NO 1
<211> LENGTH: 47
<212> TYPE: DNA
<213> ORGANISM: Homo sapiens

<400> SEQUENCE: 1
ggtacctcgc gactcgagaa aagagatgca cacaagagtg aggttgc                47

<210> SEQ ID NO 2
<211> LENGTH: 35
<212> TYPE: DNA
<213> ORGANISM: Homo sapiens

<400> SEQUENCE: 2
gacgtcaagc ttgcacactt gagtctctgt ttggc                             35

<210> SEQ ID NO 3
<211> LENGTH: 638
<212> TYPE: DNA
<213> ORGANISM: Homo sapiens

<400> SEQUENCE: 3
ggtacctcgc gactcgagaa aagagatgca cacaagagtg aggttgctca tcggtttaaa    60
gatttgggag aagaaaattt caaagccttg gtgttgattg cctttgctca gtatcttcag   120
cagtgtccat ttgaagatca tgtaaaatta gtgaatgaag taactgaatt tgcaaaaaca   180
tgtgtagctg atgagtcagc tgaaaattgt gacaaatcac ttcatacccc ttttggagac   240
aaattatgca cagttgcaac tcttcgtgaa acctatggtg aaatggctga ctgctgtgca   300
aaacaagaac ctgagagaaa tgaatgcttc ttgcaacaca agatgacaa cccaaacctc    360 ccccgattgg tgagaccaga ggttgatgtg atgtgcactg ctttcatga caatgaagag   420 acattttga aaaaatactt atatgaaatt gccagaagac atccttactt ttatgccccg   480
gaactccttt tctttgctaa aaggtataaa gctgctttta cagaatgttg ccaagctgct   540
gataaagctg cctgcctgtt gccaaagctc gatgaacttc gggatgaagg gaaggcttcg   600
tctgccaaac agagactcaa atgtgcaagc ttgacgtc                          638

<210> SEQ ID NO 4
<211> LENGTH: 39
<212> TYPE: DNA
<213> ORGANISM: Homo sapiens

<400> SEQUENCE: 4
```

```
gacgtcaagc ttacaagatg cacacaagag tgaggttgc                           39
```

<210> SEQ ID NO 5
<211> LENGTH: 27
<212> TYPE: DNA
<213> ORGANISM: Homo sapiens

<400> SEQUENCE: 5

```
gacgtcctgc agactggcac acttgag                                        27
```

<210> SEQ ID NO 6
<211> LENGTH: 634
<212> TYPE: DNA
<213> ORGANISM: Homo sapiens

<400> SEQUENCE: 6

```
gacgtcaagc ttacaagatg cacacaagag tgaggttgct catcggttta aagatttggg    60
agaagaaaat ttcaaagcct tggtgttgat tgcctttgct cagtatcttc agcagtgtcc   120
atttgaagat catgtaaaat tagtgaatga agtaactgaa tttgcaaaaa catgtgtagc   180
tgatgagtca gctgaaaatt gtgacaaatc acttcatacc cttttttggag acaaattatg   240
cacagttgca actcttcgtg aaacctatgg tgaaatggct gactgctgtg caaaacaaga   300
acctgagaga aatgaatgct tcttgcaaca caaagatgac aacccaaacc tcccccgatt   360
ggtgagacca gaggttgatg tgatgtgcac tgcttttcat gacaatgaag agacattttt   420
gaaaaaatac ttatatgaaa ttgccagaag acatccttac ttttatgccc cggaactcct   480
tttctttgct aaaaggtata aagctgcttt tacagaatgt tgccaagctg ctgataaagc   540
tgcctgcctg ttgccaaagc tcgatgaact tcgggatgaa gggaaggctt cgtctgccaa   600
acagagactc aaatgtgcca gtctgcagga cgtc                               634
```

<210> SEQ ID NO 7
<211> LENGTH: 35
<212> TYPE: DNA
<213> ORGANISM: Homo sapiens

<400> SEQUENCE: 7

```
gacgtcctgc aggatgcaca caagagtgag gttgc                               35
```

<210> SEQ ID NO 8
<211> LENGTH: 44
<212> TYPE: DNA
<213> ORGANISM: Homo sapiens

<400> SEQUENCE: 8

```
cacgtgcagc tggaattctt attggagact ggcacacttg agtc                     44
```

<210> SEQ ID NO 9
<211> LENGTH: 645
<212> TYPE: DNA
<213> ORGANISM: Homo sapiens

<400> SEQUENCE: 9

```
gacgtcctgc aggatgcaca caagagtgag gttgctcatc ggtttaaaga tttgggagaa    60
gaaaatttca agccttggt gttgattgcc tttgctcagt atcttcagca gtgtccattt   120
gaagatcatg taaaattagt gaatgaagta actgaatttg caaaaacatg tgtagctgat   180
gagtcagctg aaaattgtga caaatcactt cataccctt ttggagacaa attatgcaca   240
gttgcaactc ttcgtgaaac ctatggtgaa atggctgact gctgtgcaaa acaagaacct   300
```

```
gagagaaatg aatgcttctt gcaacacaaa gatgacaacc caaacctccc ccgattggtg      360
agaccagagg ttgatgtgat gtgcactgct tttcatgaca atgaagagac atttttgaaa      420
aaatacttat atgaaattgc cagaagacat ccttactttt atgccccgga actccttttc      480
tttgctaaaa ggtataaagc tgcttttaca gaatgttgcc aagctgctga taaagctgcc      540
tgcctgttgc caaagctcga tgaacttcgg gatgaaggga aggcttcgtc tgccaaacag      600
agactcaaat gtgccagtct ccaataagaa ttccagctgc acgtg                      645

<210> SEQ ID NO 10
<211> LENGTH: 23
<212> TYPE: DNA
<213> ORGANISM: Homo sapiens

<400> SEQUENCE: 10
ggtacctcgc gactcgagaa aag                                               23

<210> SEQ ID NO 11
<211> LENGTH: 18
<212> TYPE: DNA
<213> ORGANISM: Homo sapiens

<400> SEQUENCE: 11
cacgtgcagc tggaattc                                                     18
```

PROTEIN CONTAINING SERUM ALBUMIN DOMAIN

BACKGROUND OF THE INVENTION

The present invention relates to a protein containing a serum albumin domain. The present invention more specifically relates to a protein having an enhanced functional activity or activities selected from among the various functional activities of the domains of serum albumin including antibacterial activity, antioxidative effect, inflammation inhibitory effect, in vivo substance transporting action, and enzymatic activity. Such a protein is provided by producing proteins of various combinations of serum albumin domains by gene recombinant technology.

BACKGROUND ART

Human serum albumin (HSA) is a main protein found in the serum of an adult, is produced in the liver, and has a function as a carrier for transporting various serum molecules. In addition, the albumin has an important role in maintaining at a normal level a plasma colloid osmotic pressure caused by a solute (colloid) which cannot pass through pores of a capillary vessel, to maintain a liquid content in blood. Therefore, the albumin has been used for treatment of various conditions associated with a liquid loss from a blood vessel, including administration for surgery, shock, burn, and a low protein blood disease that causes an edema.

Meanwhile, pharmaceutical preparations using albumin derived from the blood may be contaminated with an unknown virus. Thus, the use thereof for the human body has caused safety problems. However, a method of producing serum albumin by a microorganism transformed by gene recombinant technology has been already proposed (see JP 58-056684 A and JP 05-292993 A), and thus, a safe serum albumin preparation may be provided.

The serum albumin has various kinds of functions including an antibacterial activity, an antioxidative effect, an inflammation inhibitory effect, an in vivo substance transporting action, and an enzymatic activity in addition to the functions described above. Therefore, the serum albumin produced by gene recombinant technology is expected to be used as an excellent drug administration carrier or the like utilizing those functions in medical treatment. The serum albumin is a protein having a single stranded structure of 585 amino acids and is composed of three homologous domains. Most of the various functions of the serum albumin are presumably localized in the domains.

However, a relationship between the various activities of the serum albumin and the respective domains has not been clarified. A system for efficiently expressing the serum albumin on a domain basis has never been established.

An object of the present invention is to provide a protein having an enhanced functional activity or activities selected from among the various functional activities of serum albumin including antibacterial activity, antioxidative effect, inflammation inhibitory effect, in vivo substance transporting action, and enzymatic activity.

SUMMARY OF THE INVENTION

The inventors of the present invention have established an expression system, which is capable of preparing a DNA sequence encoding each domain of serum albumin composed of domains I, II, and III, transforming a host cell using a vector containing such a DNA sequence, and producing a protein containing the serum albumin domain in the host cell. Further, the inventors of the present invention have conducted a functional analysis on each domain. As a result, the inventors of the present invention have found that a specific domain is responsible for most of specific biological activities of albumin. In addition, the inventors of the present invention have found that a protein having various enhanced functional activities of albumin can be provided by producing a protein containing a large amount of the specific domain by gene recombinant technology, and have completed the present invention. In particular, the inventors of the present invention have found out that albumin domain I has high antioxidative ability while showing low enzyme activity. Therefore, a protein containing domain I can provide an enhanced antioxidative effect.

As a result of the investigation of the binding property of three site I markers (subsite Ia, Ib, Ic), only subsite Ic ligand shows binding with domain II though the binding strength is weak. The site II drugs show a binding property with domain II in a ratio of 60 to 80% compared to the wild type albumin. However an esterase-like activity is shown to be remarkably high in the domain III but significantly less than a wild type albumin. An enolase-like activity is not shown in any domain at pH 7.2 but is shown in the domain II at pH 9.2. Further, it is interesting that an antioxidative effect of domain I is substantially similar to that of the wild type albumin. Moreover, each domain reflects a molecular weight to show a large clearance in the kidney. As domain I shows high antioxidant property and low enzymatic activity, it is expected that a protein genetically modified to contain albumin domain I will be applied to a drug delivery system. A protein containing a plurality of amino acid sequences corresponding to domain I will show enhanced antioxidant property.

Figure 1:
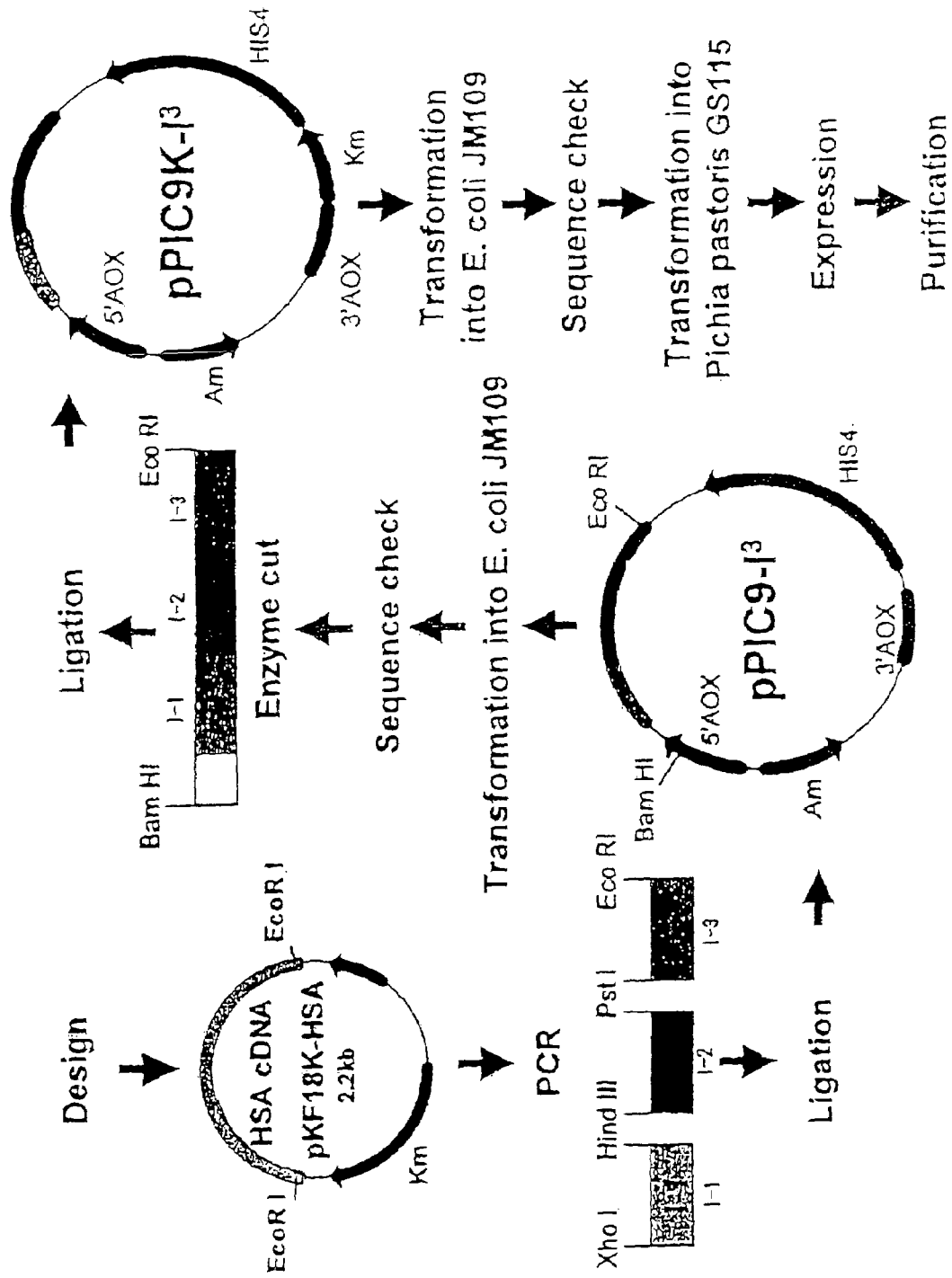
FIG. 1 is an explanatory diagram showing an outline of procedures for production of a human serum albumin domain I trimer of Example 1.

The features of the present invention include: an engineered gene that encodes a protein containing a serum albumin domain, which contains at least one gene that encodes any domain selected from domains I, II, and III of serum albumin; and a protein produced by gene recombinant technology using such a gene.

That is, the present invention provides:

(1) A protein including at least one domain selected from domains I, II, and III of serum albumin and having a different structure from the structure of native albumin;

(2) A protein according to the above item (1), in which one or two domains selected from domains I, II, and III of serum albumin is or are each included in a larger amount compared with the amount of each of other domains or domain;

(3) A protein according to the above item (1), in which only one or two domains selected from domains I, II, and III of serum albumin is or are included;

(4) A protein according to the above item (1), in which only one domain selected from domains I, II, and III of serum albumin is included;
(5) A protein according to the above item (1), in which only domain I of serum albumin is included;
(6) A protein according to the above item (1), in which the serum albumin comprises human serum albumin;
(7) A pharmaceutical preparation including the protein according to the above item (1);
(8) A DNA fragment, which is different from a DNA fragment that encodes native albumin, including a DNA sequence encoding at least one domain selected from domains I, II, and III of serum albumin;
(9) A DNA fragment according to the above item (8), in which a DNA sequence encoding each of one or two domains selected from domains I, II, and III of serum albumin is included in a larger amount compared with the amount of each of DNA sequences encoding other domains;
(10) A DNA fragment according to the above item (8), in which a restriction enzyme cleavage site intervenes between the DNA sequences that encode the respective domains of serum albumin;
(11) A recombinant vector including the DNA sequence according to item (8);
(12) A transformant produced by transforming a host cell by using the recombinant vector according to the above item (11);
(13) A method of producing the protein according to the above item (1), including the steps of constructing a recombinant vector by incorporating the DNA fragment according to the above item (8), transforming a host cell by using the recombinant vector and collecting a protein produced by incubating the transformed cell; and
(14) A method for producing the DNA fragment according to item (8), including the steps of introducing a DNA fragment in which a restriction enzyme cleavage site intervenes between DNA sequences that encode respective domains of serum albumin into a vector, transforming a host cell having high proliferation potency with the recombinant vector, incubating a transformant obtained, extracting DNA from proliferated cells and cleaving the DNA fragment with a restriction enzyme.

The protein of the present invention is capable of enhancing the specific activity of albumin. Thus, any activity can be selected as desired from an antioxidative effect, a substance transporting ability, and so on, and the protein can be applied effectively to a human body or the like. In addition, as the protein is produced by gene recombinant technology, there is no risk of contamination from any unknown virus or the like, which is a problem peculiar to blood preparations. Thus, the protein can be used safely for a human body. Furthermore, the protein is composed of ingredients originally found in the living body, so that the administration thereof causes little influence such as side effects on a human body.

In the present invention, a DNA fragment, in which a restriction cleavage site intervenes between DNA sequences that encode respective domains of serum albumin, is introduced into a host cell having high proliferation potency. Then, the resulting transformant is incubated, and DNA is extracted from proliferated cells. The DNA is cleaved with a specific restriction enzyme to selectively and efficiently obtain a DNA fragment that contains a DNA sequence encoding a target albumin domain.

A protein of the present invention is a protein containing at least one domain selected from domains I, II, and III of serum albumin and having a different structure from that of native albumin. The protein preferably contains one or two domains selected from domains I, II, and III of serum albumin in a larger amount than those of other domains. The protein more preferably contains only one or two domains selected from domains I, II, and III of serum albumin. The protein most preferably contains only one domain selected from domains I, II, and III of serum albumin. For obtaining a protein having an antioxidative effect, the protein preferably contains domain I of serum albumin. In addition, the domain I has NO-donor ability, and thus, the protein preferably contains the domain I for enhancing a vasohypotonic effect. Furthermore, the protein preferably contains domain III for enhancing an esterase-like action.

Furthermore, the protein of the present invention has a peptide sequence and a conformation, which are different from those of the native albumin, to thereby provide a protein having new activity different from that of native albumin. The protein of the present invention encompasses proteins composed of domains I, II, and III of albumin and having a different order of the respective domain sequences from that of native albumin. In the present invention, the serum albumin is preferably human serum albumin.

The DNA fragment used in the present invention is a DNA fragment, which is different from a DNA fragment encoding native albumin, containing a DNA sequence encoding at least one domain selected from domains I, II, and III of serum albumin. The DNA sequence encoding each of one or two of domains selected from domains I, II, and III of serum albumin is preferably included in a larger amount compared with those of DNA sequences that encode the other domains. In addition, the DNA fragment is preferably a DNA fragment in which a restriction enzyme cleavage site intervenes between the DNA sequences encoding the respective domains of serum albumin.

As a method of incorporating the above DNA fragment into a vector, various known methods can be used. For instance, there is used a method of adding ligase to a mixture solution of the DNA fragment treated with various restriction enzymes and the vector to connect the vector and the DNA fragment. The vector used may be any vector employed in gene recombinant technology, and a plasmid vector is generally used.

Subsequently, the above recombinant vector is introduced into a host cell to obtain a transformant. A method of introducing a recombinant vector into the host cell may be any of the methods conventionally used in the art including a competent method, a protoplast method, a calcium phosphate a co-precipitation method, an electroporation method, a microinjection method, a liposome fusion method, and a particle gun method. An arbitrary method may be applied depending on the host used. When *Schizo Saccharomyces pombe* is used as a host, a lithium acetate method (K. Okazaki et al., Nucleic Acids Res., 18, 6485-6489(1990)), for example, can be used for efficiently obtaining a transformant.

The host cells used are preferably eukaryotic cells. Examples of the eukaryotic cells include *Phichia pastoris, Saccharomyces cerevisiae,* and *Shizo Saccharomyces pombe. Phichia pastoris* is preferred.

The thus-obtained transformant is incubated, and a protein is then produced in a culture. The protein is isolated by a known method and optionally purified to obtain the target protein.

A medium for incubating the transformant is one of the known media including: a nutrient medium such as a YPD medium; a minimal medium such as an MB medium; a BMMY medium; and a BMGY medium. The transformant is incubated generally at about 16 to 46° C., preferably about 25 to 37° C., for about 8 to 168 hours, preferably about 24 to 120 hours. The transformant may be incubated by a shaking or stationary culture, or additionally with stirring and aeration if necessary.

Examples of a known method of isolating and purifying a fusion protein produced in the culture include: a method using a difference in solubility such as salt precipitation or solvent precipitation; a method using a difference in molecular weight such as dialysis, ultrafiltration, or gel-electrophoresis; a method using a difference in charge such as ion-exchange chromatography; a method using specific affinity such as affinity chromatography; a method using a difference in hydrophobicity such as reversed-phase high performance liquid chromatography; and a method using a difference in isoelectric point such as isoelectric focusing.

Examples of a known method of identifying an isolated and purified protein include a western blotting method and an activity measurement method. In addition, the purified protein can be subjected to an amino acid analysis, an amino terminal analysis, a primary structure analysis, or the like, to thereby clarify its structure.

EXAMPLE 1

FIG. 1 shows an outline of procedures for preparing a human serum albumin domain I trimer of Example 1.

Amplification of DNA Fragment Encoding Human Serum Albumin Domain I

Figure 2:
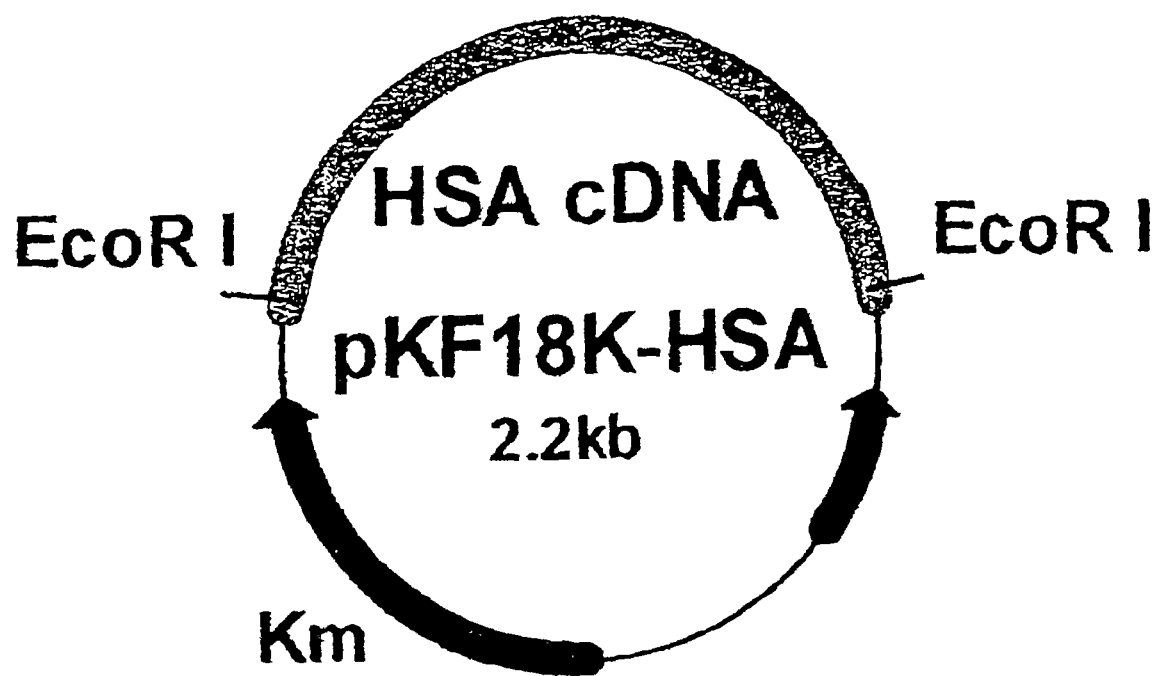
FIG. 2 is a schematic diagram of pKF18K-HAS.
Figure 3:
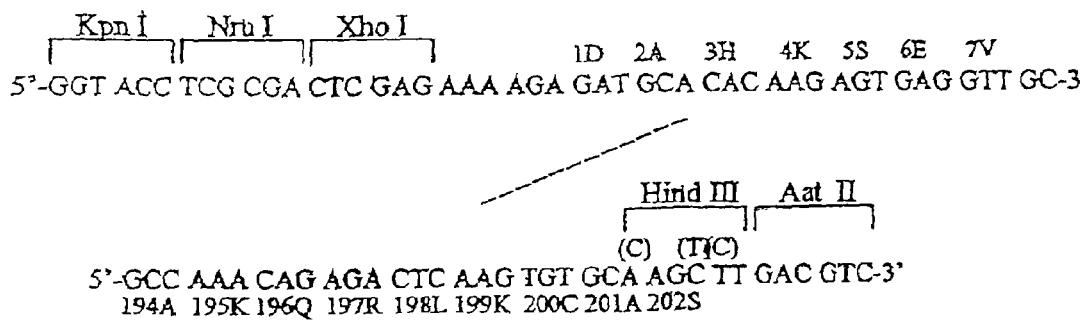
FIG. 3 is a schematic diagram of DNA fragment I-1 in Example 1.
Figure 4:
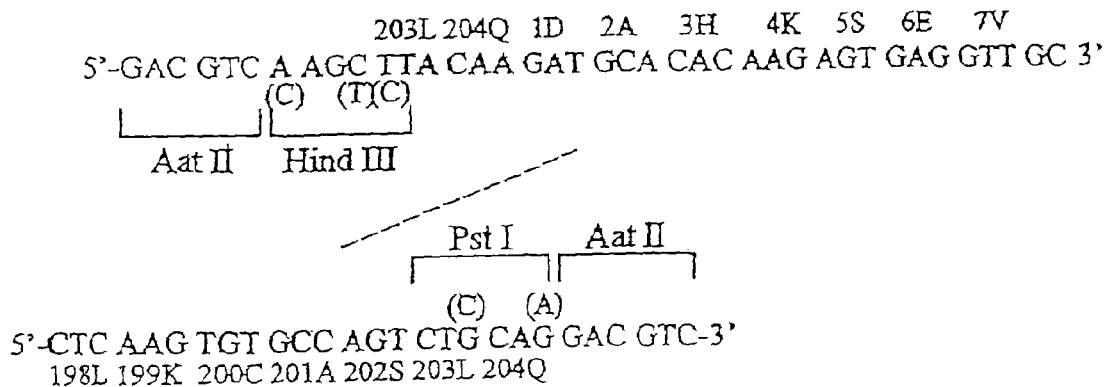
FIG. 4 is a schematic diagram of DNA fragment I-2 in Example 1.
Figure 5:
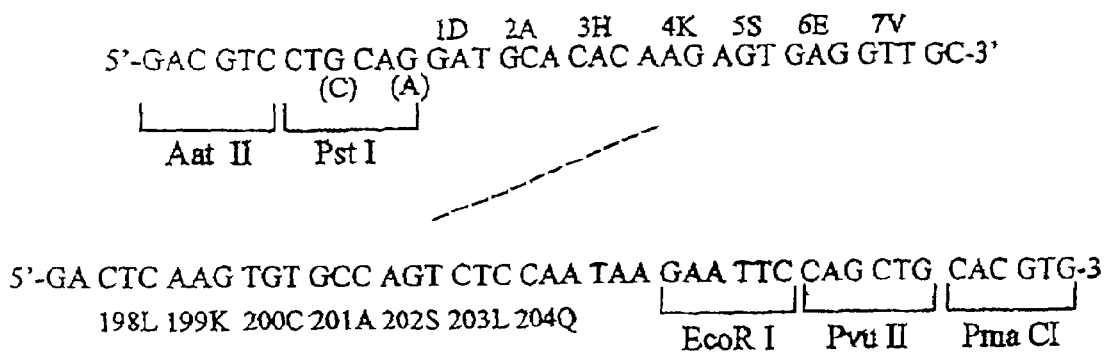
FIG. 5 is a schematic diagram of DNA fragment I-3 in Example 1.

A plasmid prepared by incorporating a gene encoding human serum albumin into a plasmid pKF18K (hereinafter, pKF18K-HAS, available from TonenGeneral Sekiyu K.K.) (see FIG. 2) was used as a template. A sense primer of SEQ. ID. No. 1 and an anti-sense primer of SEQ ID NO:2, a sense primer of SEQ ID NO:3 and an anti-sense primer of SEQ ID NO:4, and a sense primer of SEQ. ID. NO:5 and an anti-sense primer of SEQ ID NO:6 were used as synthetic primers to carry out PCR using DNA polymerase (KOD-plus-, available from Toyobo Co., Ltd.). As reaction conditions for PCR, DNA was treated at 94° C. for 10 minutes, subjected to a series of reactions of denaturing (94° C., 1 min.), annealing (64° C., 1 min.), and extension (72° C., 1 min.) for 30 cycles, and then treated at 72° C. for 3 minutes. DNA fragments, to which DNA sequences having restriction enzyme cleavage sites on the 3'-end and 5'-end portions of DNA sequences encoding domain I of human serum albumin were added, were amplified by PCR. Therefore, a DNA fragment amplified by the sense primer of SEQ ID NO:1 and the anti-sense primer of SEQ ID NO:2 (hereinafter, I-1, see SEQ ID NO:3 and FIG. 3), a DNA fragment amplified by the sense primer of SEQ ID NO:4 and the anti-sense primer of SEQ ID NO:5 (hereinafter, I-2, see SEQ. ID. NO:6 and FIG. 4), and a DNA fragment amplified by the sense primer of SEQ ID NO:7 and the anti-sense primer of SEQ ID NO: 9 (hereinafter, I-3, see SEQ ID NO:9 and FIG. 5) were obtained.

Ligation of DNA Fragments Encoding Human Serum Albumin Domain I

For ligating the DNA fragments I-1, I-2, and I-3, the DNA fragments were subjected to restriction enzyme treatment, respectively. The DNA fragment I-1 was cleaved with restriction enzyme Hind III (GIBCO), I-2 was cleaved with the restriction enzymes Pst I and Hind III (GIBCO), and I-3 was cleaved with the restriction enzyme Pst I. The resulting fragments were purified through phenol extraction and ethanol precipitation, respectively. After that, a DNA fragment (hereinafter, $I^3$) having the DNA fragments I-1, I-2, and I-3 ligated was obtained through a ligation reaction at 16° C. for 2 hours using a DNA ligation kit (DNA Ligation Kit Ver. 1, manufactured by Takara Shuzo Co., Ltd.). The DNA fragment after the ligation reaction was subjected to thermal treatment at 70° C. for 10 minutes and then purified through phenol extraction and ethanol precipitation again, followed by agarose gel electrophoresis and gel extraction using a gel extraction kit (QIAquik Gel Extraction Kit, manufactured by QIAGEN GmbH).

Next, PCR using DNA polymerase (KOD-plus-, available from Toyobo Co., Ltd.) was carried out using the DNA fragment $I^3$ after the gel extraction as a template and a sense primer of SEQ ID NO: 10 and an anti-sense primer of SEQ ID NO:11 as synthetic primers. As the reaction conditions for PCR, DNA was treated at 94° C. for 2 minutes, subjected to a series of reactions of denaturing (94° C., 15 sec.), annealing (63° C., 30 sec.), and extension (68° C., 2 min.) for 30 cycles, and then treated at 68° C. for 5 minutes. The DNA fragment $I^3$ having cleavage sites for the restriction enzymes Xho I and Eco RI on 3'-end and 5'-end portions was amplified, and a sufficient amount thereof could be synthesized.

Ligation of DNA Fragment and Plasmid

The DNA fragment $I^3$ amplified by PCR was purified through phenol extraction, ethanol precipitation, and gel extraction, followed by cleavage with the restriction enzymes Xho I and Eco RI (available from Takara Shuzo Co., Ltd.). Meanwhile, a plasmid pPIC9 was cleaved with the restriction enzymes Xho I and Eco RI (available from Takara Shuzo Co., Ltd.) and purified through phenol extraction and ethanol precipitation. The DNA fragment $I^3$ and the plasmid pPIC9 after the restriction enzyme treatment were subjected to agarose electrophoresis, and bands corresponding to the respective DNA fragments were cut out, followed by gel extraction using a gel extraction kit (QIAquik Gel Extraction Kit, manufactured by QIAGEN GmbH). After the gel extraction, the DNA fragment $I^3$ and the plasmid pPIC9 were mixed and subjected to a ligation reaction at 16° C. for 4 hours using a DNA ligation kit (DNA ligation Kit Ver. 1, manufactured by Takara Shuzo Co., Ltd.), to thereby prepare a plasmid (hereinafter, pPIC9-$I^3$) having the DNA fragment $I^3$ incorporated into the plasmid pPIC9.

Next, the plasmid pPIC9-$I^3$ was introduced into *E. coli* JM109, and the resulting transformant was incubated. Then, a plasmid was extracted and purified from a culture solution using a plasmid purification kit (QIAprep Sin Miniprep Kit, available from QIAGEN GmbH), and the amplification of the target plasmid pPIC9-$I^3$ was confirmed. The confirming method involved: double cleavage with the restriction enzymes Xho I and Eco RI (available from Takara Shuzo Co., Ltd.) and double cleavage with the restriction enzymes Hind III and PstI (GIBCO), to thereby prepare a restriction map. Simultaneously, the DNA sequence was decoded using a DNA sequencer (ABI Prism 310 Genetic Analyzer, manufactured by Perkin-Elmer Applied Biosystems Inc.).

Expression of Human Serum Albumin Domain I Trimer

The plasmid pPIC9-$I^3$ was cleaved with the restriction enzyme Sal I and purified through phenol extraction and ethanol precipitation, followed by transformation through introduction of the plasmid pPIC9-$I^3$ into *Pichia pastoris* GS115 by an electroporation method using an electroporation system (Gene Pulser II Electroporation System, manufactured by Bio-Rad Laboratories, Inc.). The resulting transformant was screened, and only positive clones exhibiting G418 resistance were incubated in a BMMY liquid medium. Then, the expression of an albumin protein was confirmed, and the transformant was then stored in glycerol.

Purification of Human Serum Albumin Domain I Timer

The transformed *Pichia pastoris* GS115 was incubated in a BMGY liquid medium for 48 hours and then incubated in a BMMY medium for 96 hours while adding 1% methanol every 12 hours. Yeast cells were isolated from the culture solution by centrifugation (6,000 g × 10 min.), and a culture supernatant was then filtered through a 0.22-im filter and then filtered using a purification column (Blie affinity CL-6B column).

The protein of the present invention is expected to be applied to DDS by performing a protein engineering modification on the protein. In particular, the protein of the present invention can be used effectively as a drug administration carrier used for improving retention in blood, without the risk of virus contamination.

Furthermore, a protein additionally having an antibacterial activity can be produced by producing a protein having a nitroso albumin variant added. The nitroso albumin variant is obtained through nitrosation of an albumin variant having one or more amino acid residues of constitutive amino acids in the protein of the present invention.

What is claimed is:

1. An isolated or purified protein comprising two or three of domain I of serum albumin, having a structure different from a structure of serum albumin and showing an enhanced antioxidative effect or an enhanced vasohypotonic effect relative to serum albumin.

2. An isolated or purified protein according to claim 1, wherein the protein is used as a drug administration carrier.

3. A pharmaceutical preparation comprising the protein according to claim 1.

4. The protein according to claim 1, wherein each domain I is followed by, in order, domain II and/or domain III of the native serum albumin.

* * * * *